(12) United States Patent
Michelson

(10) Patent No.: US 7,462,195 B1
(45) Date of Patent: *Dec. 9, 2008

(54) ARTIFICIAL LUMBAR INTERBODY SPINAL IMPLANT HAVING AN ASYMMETRICAL LEADING END

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/553,573

(22) Filed: Apr. 19, 2000

(51) Int. Cl.
A61F 2/44 (2006.01)
(52) U.S. Cl. .................................. 623/17.11
(58) Field of Classification Search .............. 623/17.11, 623/17.16
See application file for complete search history.

(56) References Cited

U.S. PATENT DOCUMENTS

| | | |
|---|---|---|
| 2,677,369 A | 5/1954 | Knowles |
| 3,426,364 A | 2/1969 | Lumb |
| 3,848,601 A | 11/1974 | Ma et al. |
| 3,867,728 A | 2/1975 | Stubstad et al. |
| 3,875,595 A | 4/1975 | Froning |
| 3,905,047 A | 9/1975 | Long |
| D245,259 S | 8/1977 | Shen |
| 4,070,514 A | 1/1978 | Eatherly |
| 4,309,777 A | 1/1982 | Patil |
| 4,349,921 A | 9/1982 | Kuntz |
| 4,501,269 A | 2/1985 | Bagby |
| RE31,865 E | 4/1985 | Roux |
| 4,599,086 A | 7/1986 | Doty |
| 4,636,217 A | 1/1987 | Ogilvie et al. |
| 4,714,469 A | 12/1987 | Kenna |
| 4,743,256 A | 5/1988 | Brantigan |
| 4,759,766 A | 7/1988 | Buettner-Janz et al. |
| 4,759,769 A | 7/1988 | Hedman et al. |
| 4,820,305 A | 4/1989 | Harms et al. |
| 4,834,757 A | 5/1989 | Brantigan |
| 4,863,476 A | 9/1989 | Shepperd |

(Continued)

FOREIGN PATENT DOCUMENTS

DE 35 05 567 5/1986

(Continued)

OTHER PUBLICATIONS

Muschler, et al.; The Biology of Spinal Fusion; Spinal Fusion Science and Technique, Cotler and Cotler, pp. 9-13.

(Continued)

*Primary Examiner*—Bruce E Snow
(74) *Attorney, Agent, or Firm*—Martin & Ferrano, LLP

(57) ABSTRACT

An artificial interbody spinal implant adapted for placement across an intervertebral space formed across the height of a disc space between two adjacent vertebral bodies is disclosed. The implant has an asymmetrical leading end adapted to sit upon the more peripheral areas, such as the apophyseal rim and the apophyseal rim area, of the vertebral end plate region of the vertebral bodies without protruding therefrom. The asymmetrical leading end allows for the safe use of an implant of maximum length for the implantation space into which it is installed. The implant can also include an asymmetric trailing end adapted to sit upon the more peripheral areas of the vertebral end plate region of the vertebral bodies.

42 Claims, 7 Drawing Sheets

U.S. PATENT DOCUMENTS

| | | |
|---|---|---|
| 4,863,477 A | 9/1989 | Monson |
| 4,877,020 A | 10/1989 | Vich |
| 4,878,915 A | 11/1989 | Brantigan |
| 4,904,261 A | 2/1990 | Dove et al. |
| 4,911,718 A | 3/1990 | Lee et al. |
| 4,936,848 A | 6/1990 | Bagby |
| 4,955,908 A | 9/1990 | Frey et al. |
| 4,961,740 A | 10/1990 | Ray et al. |
| 5,015,247 A | 5/1991 | Michelson |
| 5,015,255 A | 5/1991 | Kuslich |
| 5,026,373 A | 6/1991 | Ray et al. |
| 5,047,055 A | 9/1991 | Bao et al. |
| 5,055,104 A | 10/1991 | Ray |
| 5,059,193 A | 10/1991 | Kuslich |
| 5,062,845 A | 11/1991 | Kuslich et al. |
| 5,071,437 A | 12/1991 | Steffee |
| 5,122,130 A | 6/1992 | Keller |
| 5,123,926 A | 6/1992 | Pisharodi |
| 5,171,278 A | 12/1992 | Pisharodi |
| 5,192,327 A | 3/1993 | Brantigan |
| 5,246,458 A | 9/1993 | Graham |
| 5,258,031 A | 11/1993 | Salib et al. |
| 5,290,312 A | 3/1994 | Kojimoto et al. |
| 5,306,309 A | 4/1994 | Wagner et al. |
| 5,370,697 A | 12/1994 | Baumgartner |
| 5,397,364 A | 3/1995 | Kozak et al. |
| 5,425,772 A | 6/1995 | Brantigan |
| 5,443,514 A | 8/1995 | Steffee |
| 5,458,638 A | 10/1995 | Kuslich et al. |
| 5,489,307 A | 2/1996 | Kuslich et al. |
| 5,489,308 A | 2/1996 | Kuslich et al. |
| 5,522,899 A | 6/1996 | Michelson |
| 5,571,109 A | 11/1996 | Bertagnoli |
| 5,593,409 A | 1/1997 | Michelson |
| 5,609,635 A | 3/1997 | Michelson |
| 5,609,636 A | 3/1997 | Kohrs et al. |
| 5,645,598 A | 7/1997 | Brosnahan, III |
| 5,658,337 A | 8/1997 | Kohrs et al. |
| 5,669,909 A | 9/1997 | Zdeblick et al. |
| 5,683,463 A | 11/1997 | Godefroy et al. |
| 5,766,252 A | 6/1998 | Henry et al. |
| 5,782,919 A | 7/1998 | Zdeblick et al. |
| D397,439 S | 8/1998 | Koros et al. |
| 5,800,547 A | 9/1998 | Schäfer et al. |
| 5,800,550 A | 9/1998 | Sertich |
| 5,814,084 A | 9/1998 | Grivas et al. |
| 5,861,041 A | 1/1999 | Tienboon |
| 5,865,845 A | 2/1999 | Thalgott |
| 5,888,227 A * | 3/1999 | Cottle ............... 623/17.16 |
| 6,033,438 A | 3/2000 | Bianchi et al. |
| 6,113,638 A * | 9/2000 | Williams et al. ........ 128/898 |
| 6,143,032 A | 11/2000 | Schafer |
| 6,174,311 B1 | 1/2001 | Branch et al. |
| 6,179,875 B1 | 1/2001 | Von Strempel |
| 6,241,770 B1 | 6/2001 | Michelson |
| 6,241,771 B1 | 6/2001 | Gresser |
| 6,245,108 B1 | 6/2001 | Biscup |
| 6,258,125 B1 | 7/2001 | Paul et al. |
| 6,277,149 B1 | 8/2001 | Boyle et al. |
| 6,350,283 B1 * | 2/2002 | Michelson ............ 623/17.11 |
| 6,610,065 B1 | 8/2003 | Branch et al. |
| 6,666,890 B2 | 12/2003 | Michelson |
| 6,984,245 B2 | 1/2006 | McGahan et al. |
| 7,022,137 B2 | 4/2006 | Michelson |
| 2006/0235519 A1 | 10/2006 | Michelson |

FOREIGN PATENT DOCUMENTS

| | | |
|---|---|---|
| EP | 0077159 | 4/1983 |
| EP | 0 179 695 | 4/1986 |
| EP | 0260044 A1 | 3/1988 |
| EP | 0307241 A2 | 3/1989 |
| EP | 0577179 A1 | 1/1994 |
| EP | 0599419 A2 | 6/1994 |
| EP | 0 627 204 | 12/1994 |
| EP | 0 637 440 | 10/1997 |
| ES | 283078 | 5/1985 |
| FR | 2 703 580 | 10/1994 |
| FR | 2703580 | 10/1994 |
| FR | 2 724 312 | 3/1996 |
| FR | 2724312 * | 3/1996 |
| JP | 57-29348 | 2/1982 |
| JP | 61-122859 | 6/1986 |
| JP | 62-155846 | 7/1987 |
| WO | WO 9214423 | 9/1992 |
| WO | WO 9301771 | 2/1993 |
| WO | 95/08964 | 4/1995 |
| WO | WO 9508964 | 4/1995 |

OTHER PUBLICATIONS

Zindrick, et al.; Lumbar Spine Fusion: Different Types and Indications; The Lumbar Spin, vol. 1, Second Edition, pp. 588-593 (1996).

Crock, H.V.; Practice of Spinal Surgery; Springer-Verlag/Wien, New York (1983).

DeBowes, R.M., et al.; Study of Bovine . . . Steel Baskets; Transactions of the 29th Annual Meeting; Orthopaedic Research Society, vol. 8, p. 407, Mar. 8-10, 1983.

Otero-Vich, Jose M.; Anterior Cervical Interbody Fusion with Threaded Cylindrical Bone; J. Neurosurg 63:750-753 . (Nov. 1985).

Butts, M.K., et al.; Biomechanical Analysis of a New Method for Spinal Interbody Fixation; 1987 Symposium, American Society of Mechanical Engineers, "Advances in Bioengineering", Boston, MA (Dec. 13-18, 1987).

Crawley et al.; A Modified Cloward's Technique for Arthrodesis of the Normal Metacarpophalangeal Joint in the Horse; Veterinary Surgery, vol. 17, No. 3, pp. 117-127 (1988).

Bagby, G.W.; Arthrodesis by the Distraction-Compression Method Using a Stainless Steel Implant; Orthopedics, vol. II, No. 6, pp. 931-934 (Jun. 1987).

Itoman, M., et al.; Banked Bone grafting for Bone Defect Repair-Clinical Evaluation of Bone Union and Graft Incorporation; J. Jpn. Orthop. Assoc. 62:461-469 (1988).

Schmitz et al.; Performance of Alloplastic Materials and Design of an Artificial Disc; the Artificial Disc, Brock, Mayer, Weigel; pp. 23-34 (1991).

Fusion of the Lumbar Spine; Anterior Monosegmental Fusion L5-S1, Atlas of Spinal Operations, Thieme, pp. 270-274 (1993).

Lumbar Spine Surgery, Techniques & Complications; History of Lumbar Spine Surgery (1994) pp. 11-15; 27; 30; 35-45; 265-268.

European Opposition Document, Nov. 27, 1995—Opposing EP Patent No. 425 542 B1 to Karlin Technology, Inc.

Laparoscopic Bone Dowel Surgical Technique; Brochure of Sofamor Danek (1995).

Laparoscopic Bone Dowel Instruments; Brochure of Sofamor Danek (1995).

Brochure of University of Florida Tissue Bank; MD-I and MD-II Custom Machine Cortical Dowels; (Circa 1996).

Brochure of University of Florida Tissue Bank; MD-III Threaded Cortical Dowel; (Circa 1996).

Glazer, P.A., et al.; Biomechanical Analysis of Multilevel Fixation Methods in the Lumbar Spine; Spine, vol. 22, No. 2, pp. 171-172 (1997).

Ray, C.D.; Spinal Interbody Fusions: A Review, Featuring New Generation Techniques; Neurosurgery Quarterly, 7(2):135-156 (1997).

A picture of a Medtronic, Sofamor Danek Display; titled "Evolving With Your Needs" (Apr. 6, 2000).

International Search Report mailed on Aug. 15, 2001 of corresponding International Application No. PCT/US01/11723, filed Apr. 19, 2001.

* cited by examiner

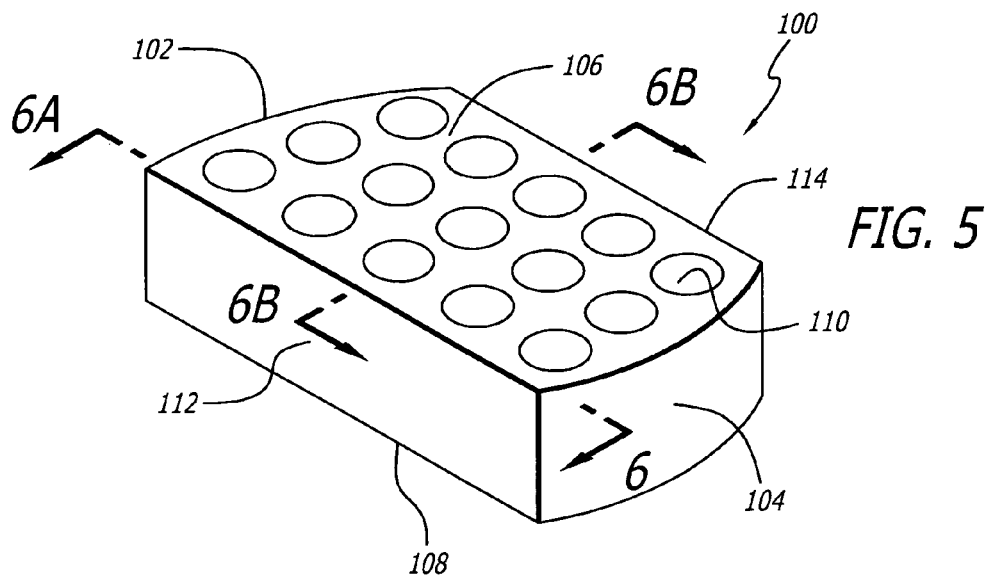
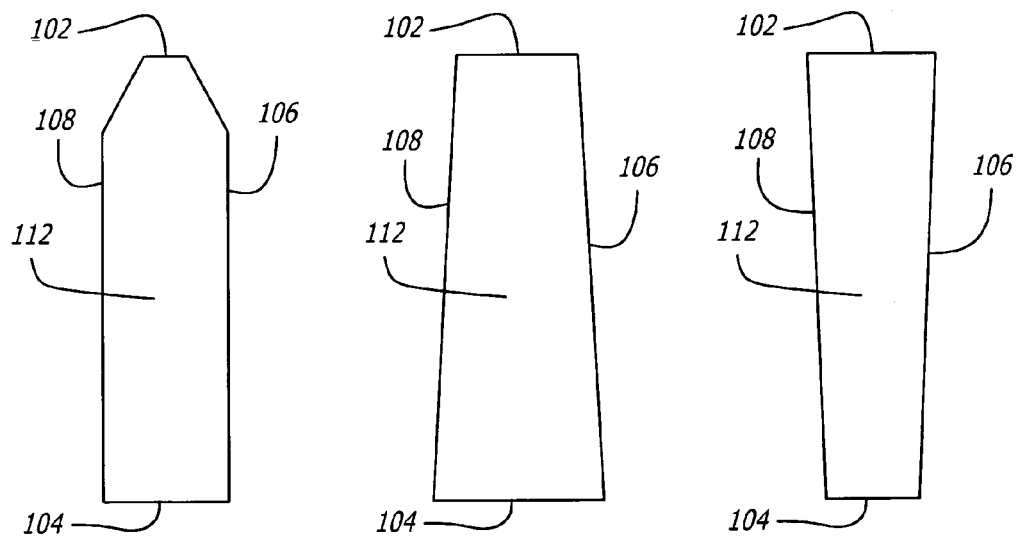
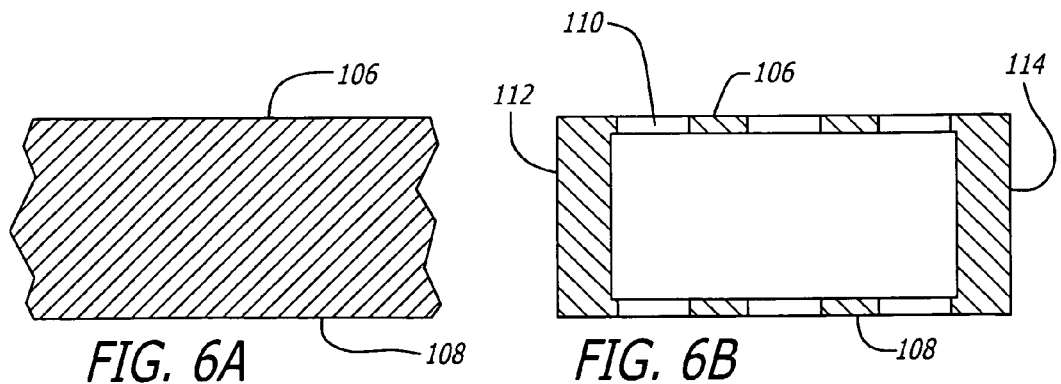

ARTIFICIAL LUMBAR INTERBODY SPINAL IMPLANT HAVING AN ASYMMETRICAL LEADING END

BACKGROUND OF THE INVENTION

1. Field of the Invention

The present invention relates generally to interbody spinal implants preferably adapted for placement in pairs side by side to either side of the midline with or without a space therebetween into a space created across the height of a disc space and between two adjacent vertebral bodies, after the removal of damaged spinal disc material, for the purpose of correcting spinal disease at that interspace. The spinal implants are made of an implant material that is other than bone and may or may not be resorbable. Where the implants are spinal fusion implants, they are adapted such that fusion occurs at least in part through the implants themselves. Where the implants are motion preserving for maintaining spinal motion, bone growth can occur at least in part into the spinal implants themselves, but not across them, and they are adapted to allow for relative motion between the vertebrae.

2. Description of the Related Art

Surgical interbody spinal fusion generally refers to the methods for achieving a bridge of bone tissue in continuity between adjacent vertebral bodies and across the disc space to thereby substantially eliminate relative motion between the adjacent vertebral bodies. The term "disc space" refers to the space between adjacent vertebral bodies normally occupied by a spinal disc.

Motion preserving implants maintain the spacing between the two adjacent vertebral bodies and allow for relative motion between the vertebrae. Bone growth from the adjacent vertebral bodies into the motion preserving implant, but not through the implant, anchors the implant to the adjacent vertebral bodies while preserving the relative motion between the vertebrae.

Spinal implants can have opposed upper and lower surfaces that are arcuate or non-arcuate transverse to the longitudinal axis of the implant along at least a portion of the length of the implant. Implants having arcuate opposed portions are adapted to be implanted across and beyond the height of the restored disc space, generally into a bore formed across the height of a disc space. Some of the advantages offered by implants with arcuate opposed portions include: 1) the installation of the implant into vascular bone made possible by the creation of a bore into the bone of the adjacent vertebral bodies; 2) the implant's geometric shape is easy to manufacturer; 3) the implant can include external threads to facilitate insertion into the implantation space; and 4) the implant provides more surface area to contact the adjacent vertebral bodies than would a flat surface. Some disadvantages associated with implants having arcuate opposed portions include: 1) the creation of a bore into the adjacent vertebral bodies to form the implantation space results in a loss of the best structural bone of the vertebral endplate; 2) the implant needs to have a larger cross section to fill the prepared implantation site which may be more difficult to install, especially from a posterior approach; and 3) the width of the implant is generally related to the height of the implant, so if the implant is for example a cylinder, the width of the implant may be a limiting factor as to the height of the implant and therefore to the possible usefulness of the implant.

Implants having non-arcuate upper and lower opposed portions may be impacted into a space resembling the restored disc space and need only be placed against a "decorticated endplate." A decorticated endplate is prepared by the surgeon to provide access to the underlying vascular bone. Some of the advantages provided by implants having non-arcuate opposed portions include: 1) preserving the best bone in the endplate region; 2) the height of the implant is independent of its width; 3) the implant can be of a geometric shape and the opposed upper and lower surfaces can be flat; 4) the implants can be installed as part of a modular unit; and 5) the implants can provide a broad surface contact. Some of the disadvantages provided by implants having non-arcuate opposed portions include: 1) the implants cannot be threaded in and must be impacted into the installation space; and 2) the recipient site may be more difficult to prepare.

Human vertebral bodies have a hard outer shell of compacted dense cancellous bone (sometimes referred to as the cortex) and a relatively softer, inner mass of cancellous bone. Just below the cortex adjacent the disc is a region of bone referred to herein as the "subchondral zone". The outer shell of compact bone (the boney endplate) adjacent to the spinal disc and the underlying subchondral zone are together herein referred to as the boney "end plate region" and, for the purposes of this application, is hereby so defined. A circumferential ring of dense bone extends around the perimeter of the endplate region and is the mature boney successor of the "apophyseal growth ring". This circumferential ring is formed of very dense bone and for the purposes of this application will be referred to as the "apophyseal rim". For the purposes of this application, the "apophyseal rim area" includes the apophyseal rim and additionally includes the dense bone immediately adjacent thereto. The spinal disc that normally resides between the adjacent vertebral bodies maintains the spacing between those vertebral bodies and, in a healthy spine, allows for the normal relative motion between the vertebral bodies.

FIG. 1 of the attached drawings shows a cross-sectional top plan view of a vertebral body V in the lumbar spine to illustrate the dense bone of the apophyseal rim AR present proximate the perimeter of the vertebral body V about the endplate region and an inner mass of cancellous bone CB. The structure of the vertebral body has been compared to a core of wet balsa wood encased in a laminate of white oak. The apophyseal rim AR is the best structural bone and is peripherally disposed in the endplate of the vertebral body.

FIG. 2 is a top plan view of a fourth level lumbar vertebral body V shown in relationship anteriorly with the aorta and vena cava (collectively referred to as the "great vessels" GV). FIG. 3 is a top plan view of a first sacral level vertebral body V shown in relationship anteriorly with the iliac arteries and veins referred to by the designation "IA-V". Because of the location of these fragile blood vessels along the anterior aspects of the lumbar vertebrae, no hardware should protrude from between the vertebral bodies and into the great vessels GV and iliac arteries and veins IA-V.

Implants for use in human spinal surgery can be made of a variety of materials not naturally found in the human body. Such materials include surgical quality metals, ceramics, plastics and plastic composites, and other such materials suitable for the intended purpose. Further, these materials may be absorbable, bioactive such as an osteogenic material, or be adapted to deliver and/or contain fusion promoting substances such as any of bone morphogenetic protein, hydroxyapatite, and genes coding for the production of bone, and/or others. Fusion implants preferably have a structure designed to promote fusion of the adjacent vertebral bodies by allowing for the growth of bone through the implant from vertebral body to adjacent vertebral body. This type of implant is intended to remain indefinitely within the patient's spine unless made of a resorbable or bioresorbable material such as bone that can be biologically replaced in the body over time such that it need not be removed as it is replaced over time and will no longer be there. Implants may be sized to have a width generally as great as the nucleus portion of the disc or as wide as the area between the limit lines LL as shown in FIG. 4. There are at least two circumstances where the use of such a wide implant is not desirable. Under these circumstances, the use of a pair of implants each having a width less than one half the width of the disc space to be fused is preferred. The first circumstance is where the implants are for insertion into the lumbar spine from a posterior approach. Because of the presence of the dural sac within the spinal canal, the insertion of a full width implant in a neurologically intact patient could not be performed from a posterior approach. The second circumstance is where the implants are for endoscopic, such as laproscopic, insertion regardless of the approach as it is highly desirable to minimize the ultimate size cross-sectionally of the path of insertion.

The ability to achieve spinal fusion is inter alia directly related to the vascular surface area of contact over which the fusion can occur, the quality and the quantity of the fusion mass, and the stability of the construct. The overall size of interbody spinal fusion implants is limited, however, by the shape of the implants relative to the natural anatomy of the human spine. For example, if such implants were to protrude from the spine they might cause injury to one or more of the proximate vital structures including the large blood vessels or neurological structures.

FIG. 4 shows a top plan view of the endplate region of a vertebral body V with the outline of a related art implant A and implant 100 of one embodiment of the present invention installed, one on each side of the centerline of the vertebral body V. The length and width of related art implant A is limited by its configuration and the vascular structures anteriorly (in this example) adjacent to the implantation space. The presence of limiting corners LC on the implant precludes the surgeon from utilizing an implant of this configuration having both the optimal width and length because the implant would markedly protrude from the spine.

Related art implants also fail to maximally sit over the best structural bone, which is located peripherally in the apophyseal rim of the vertebral body and is formed of the cortex and dense subchondral bone. The configurations of previous implants do not allow for maximizing both the vital surface area over which fusion could occur and the area available to bear the considerable loads present across the spine. Previous implant configurations do not allow for the full utilization of the apophyseal rim bone and the bone adjacent to it, located proximate the perimeter of the vertebral body to support the implants at their leading ends and to maximize the overall support area and area of contact for the implants. The full utilization of this dense peripheral bone would be ideal.

Therefore, there is a need for an interbody spinal fusion implant having opposed portions for placement toward adjacent vertebral bodies that is capable of fitting within the outer boundaries of the vertebral bodies between which the implant is to be inserted and to maximize the surface area of contact of the implant and vertebral bone. The implant should achieve this purpose without interfering with the great vessels or neurological structures adjacent to the vertebrae into which the implant is to be implanted. There exists a further need for an implant that is adapted for placement more fully on the dense cortical bone proximate the perimeter of the vertebral bodies at the implant's leading end.

SUMMARY OF THE INVENTION

The present invention relates to an artificial spinal implant formed or manufactured prior to surgery and provided fully formed to the surgeon for use in interbody fusion made of an implant material other than bone that is appropriate for the intended purpose. The implant is of a width preferably sized to be used in pairs to generally replace all or a great portion of all of the width of the nucleus portion of the disc. To that end, the width of the implant is less than half of the width of the disc space. Preferably, the implant generally has parallel side walls and is used where it is desirable to insert an implant of enhanced length without the leading lateral wall protruding from the spine.

The interbody spinal implant of the present invention is for placement between adjacent vertebral bodies of a human spine across the height of disc space between those adjacent vertebral bodies. The implant preferably does not extend beyond the outer dimensions of the two vertebral bodies adjacent that disc space, and preferably maximizes the area of contact of the implant with the vertebral bone. In a preferred embodiment, the implant has a leading end configured to conform to the anatomic contour of at least a portion of the anterior, posterior, or lateral aspects of the vertebral bodies depending on the intended direction of insertion of the implant, so as to not protrude beyond the curved contours thereof. The implant has an asymmetrical leading end modified to allow for enhanced implant length without the corner of the leading end protruding out of the disc space. As used herein, the phrase "asymmetrical leading end" is defined as the leading end of the implant lacking symmetry from side-to-side along the transverse axis of the implant when the leading end is viewed from a top elevation.

The configuration of the leading end of the implant of the present invention allows for the safe use of an implant of maximum length for the implantation space into which it is installed. Benefits derived from a longer length implant include, but are not limited to, providing a greater surface area for contacting the vertebral bodies and for carrying bone growth promoting material at the implant surface, increased load bearing support, increased stability, and increased internal volume for holding fusion promoting material and the ability to have a portion of the implant rest upon the apophyseal rim, the best structural bone of the vertebral endplate region. These fusion promoting and bone growth promoting materials may be bone, bone products, bone morphogenetic proteins, mineralizing proteins, genetic materials coding for the production of bone or any other suitable material.

The spinal implant of the present invention may also include a trailing end opposite the leading end that is configured to conform to the anatomic contour of the anterior, posterior, or lateral aspects of the vertebral bodies, depending on the direction of insertion, so as not to protrude beyond the curved contours thereof. The present invention can benefit interbody spinal fusion implants having spaced apart non-arcuate opposed surfaces adapted to contact and support opposed adjacent vertebral bodies as well as implants having spaced apart arcuate opposed surfaces adapted to penetrably engage opposed vertebral bodies. As used herein, the term "arcuate" refers to the curved configuration of the opposed upper and lower portions of the implant transverse to the longitudinal axis of the implant along at least a portion of the implant's length.

In one embodiment of the present invention, an implant adapted for insertion from the posterior approach of the spine and for achieving better, safe filling of the posterior to anterior depth of the disc space between two adjacent vertebral bodies, and the possibility of having the leading end of the implant supported by the structurally superior more peripheral bone including the apophyseal rim and the bone adjacent to it, includes opposed portions adapted to be oriented toward the bone of the adjacent vertebral bodies, a leading end for inserting into the spine, and an opposite trailing end that may be adapted to cooperatively engage a driver. In the alternative, the implant may receive a portion of the driver through the trailing end to cooperatively engage the implant from within and/or at the implant trailing end. The leading end of this embodiment of the implant of the present invention is generally configured to conform to the natural anatomical curvature of the perimeter of the anterior aspect of the vertebral bodies, so that when the implant is fully inserted and properly seated within and across the disc space the implant contacts and supports a greater surface area of the vertebral bone in contact with the implant to provide all the previously identified advantages. Moreover, at the election of the surgeon, the implant of the present invention is configured to be able to be seated upon the more densely compacted bone about the periphery of the vertebral endplates for supporting the load through the implant when installed in or across the height of the intervertebral space.

Related art bone ring implants where the implant is a circle, oval, or oblong have trailing ends that are either modified to be squared-off, or unmodified so as to remain a portion of a circle, an oval, or an oblong and have a medial side wall that is incomplete due to a portion of the medullary canal interrupting the side wall. The present invention implants have an interior facing medial side wall adapted for placement medially within the disc space with the side wall intact and substantially in the same plane and an exterior facing lateral side wall opposite to the medial side wall adapted for placement laterally. The interior and exterior facing side walls have an inner surface facing each other. The implants of the present invention also may have a mid-longitudinal axis between the medial and lateral side walls wherein the mid-longitudinal axis at the leading end extends forward further than the lateral side wall at the leading end while the medial side wall is not equal in length to the lateral side wall, but is greater in length.

In another embodiment of the present invention, an implant for insertion from the anterior approach of the spine and for achieving better filling of the anterior to posterior depth of the disc space has a leading end generally configured to better conform to the natural anatomical curvature of the perimeter of the posterior aspect of the vertebral bodies and does not protrude laterally.

In yet another embodiment of the present invention, the implant has a trailing end that is either asymmetric or symmetric from side-to-side along the transverse axis of the implant. The trailing end may be adapted to conform to the anatomical contours of the anterior or posterior aspects of the vertebral bodies. For example, an implant for insertion from the posterior or anterior approach of the spine has a leading end that is generally configured to better conform to the natural anatomical curvature of at least one of the perimeter of the anterior and posterior aspects, respectively, of the vertebral bodies and a trailing end that is generally configured to conform to the natural anatomical curvature of the opposite one of the posterior and anterior aspects, respectively, of the vertebral bodies depending on the intended direction of insertion and that does not protrude laterally from the vertebral bodies. When the implant is fully seated and properly inserted within and across the disc space, the surface area of the vertebral bone in contact with the implant is more fully utilized.

As another example, an implant in accordance with the present invention for insertion from a translateral approach to the spine and across the transverse width of the vertebral bodies has a leading end that is generally configured to better conform to the natural anatomical curvature of the perimeter of at least one of the lateral aspects, respectively, of the vertebral bodies. The implant also may have a trailing end that is generally configured to conform to the natural anatomical curvature of the opposite one of the lateral aspects, respectively, of the vertebral bodies depending on the intended direction of insertion. Implants for insertion from a translateral approach and methods for inserting implants from a translateral approach are disclosed in Applicant's U.S. Pat. Nos. 5,860,973 and 5,772,661, respectively, incorporated by reference herein.

The implant of the present invention is better able to sit upon the dense compacted bone about the perimeter of the vertebral bodies of the vertebral endplate region for supporting the load through the implant when installed in the intervertebral space. Where the spinal implant of the present invention is an interbody spinal fusion implant then it also may have at least one opening therethrough from the upper vertebral body contacting surface through to the lower vertebral body contacting surface. The opening allows for communication between the opposed upper and lower vertebrae engaging surfaces to permit for growth of bone in continuity from adjacent vertebral body to adjacent vertebral body through the implant for fusion across the disc space.

For any of the embodiments of the present invention described herein, the implant preferably includes protrusions or surface roughenings for engaging the bone of the vertebral bodies adjacent to the implant. The material of the implant is an artificial material such as titanium or one of its implant quality alloys, cobalt chrome, tantalum, or any other metal appropriate for surgical implantation and use as an interbody spinal fusion implant, or ceramic, or composite including various plastics, carbon fiber composites, or coral, and can include artificial materials which are at least in part bioresorbable. The implants may further include osteogenic materials such as bone morphogenetic proteins, or other chemical compounds, or genetic material coding for the production of bone, the purpose of which is to induce or otherwise encourage the formation of bone or fusion.

Bone for use as the base material used to form the implant is specifically excluded from the definition of artificial materials for the purpose of this application. Where the implants are for spinal fusion, it is appreciated that they may be adapted to receive fusion promoting substances within them such as cancellous bone, bone derived products, or others.

It is appreciated that the features of the implant of the present invention as described herein are applicable to various embodiments of the present invention including implants having non-arcuate or arcuate upper and lower opposed portions adapted to be oriented toward the bone of the adjacent vertebral bodies.

BRIEF DESCRIPTION OF THE DRAWINGS

FIG. 5 is a side perspective view of the outline of an implant in accordance with one embodiment of the present invention.

FIG. 5A is a side elevational view of an implant having a tapered leading end in accordance with an embodiment of the present invention.

FIG. 5B is a side elevational view of an implant having opposed portions that are generally in a converging relationship to each other from a trailing end to a leading end of the implant in accordance with an embodiment of the present invention.

FIG. 5C is a side elevational view of an implant having opposed portions that are generally in a diverging relationship to each other from a trailing end to a leading end of the implant in accordance with an embodiment of the present invention.

FIG. 6A is a partial enlarged fragmentary view along line 6A-6A of FIG. 5.

FIG. 6B is a partial enlarged fragmentary view along line 6B-6B of FIG. 5.

DETAILED DESCRIPTION OF THE INVENTION

Figure 1:
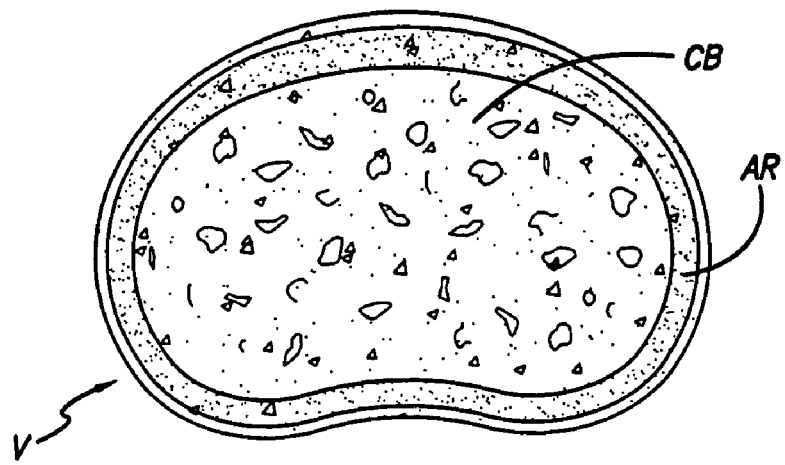
FIG. 1 is a top plan view of a horizontal cross-section through a boney endplate region of a vertebral body.
Figure 2:
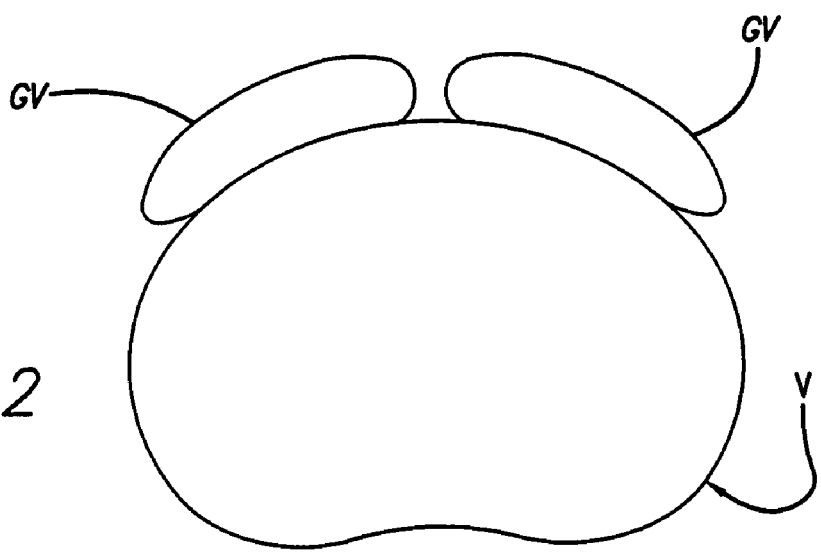
FIGS. 2-3 are top plan views of the fourth lumbar and first sacral vertebral bodies, respectively, in relationship to the blood vessels located anteriorly thereto.
Figure 3:
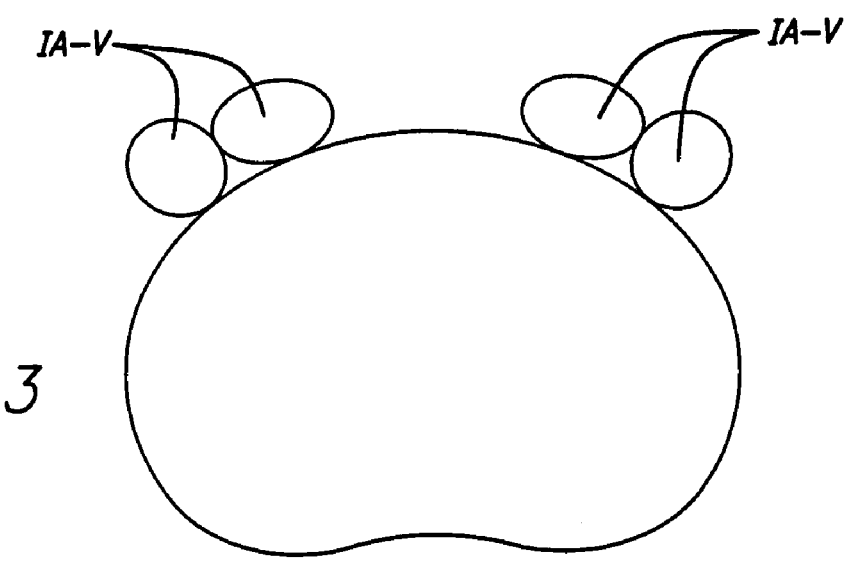
Figure 4:
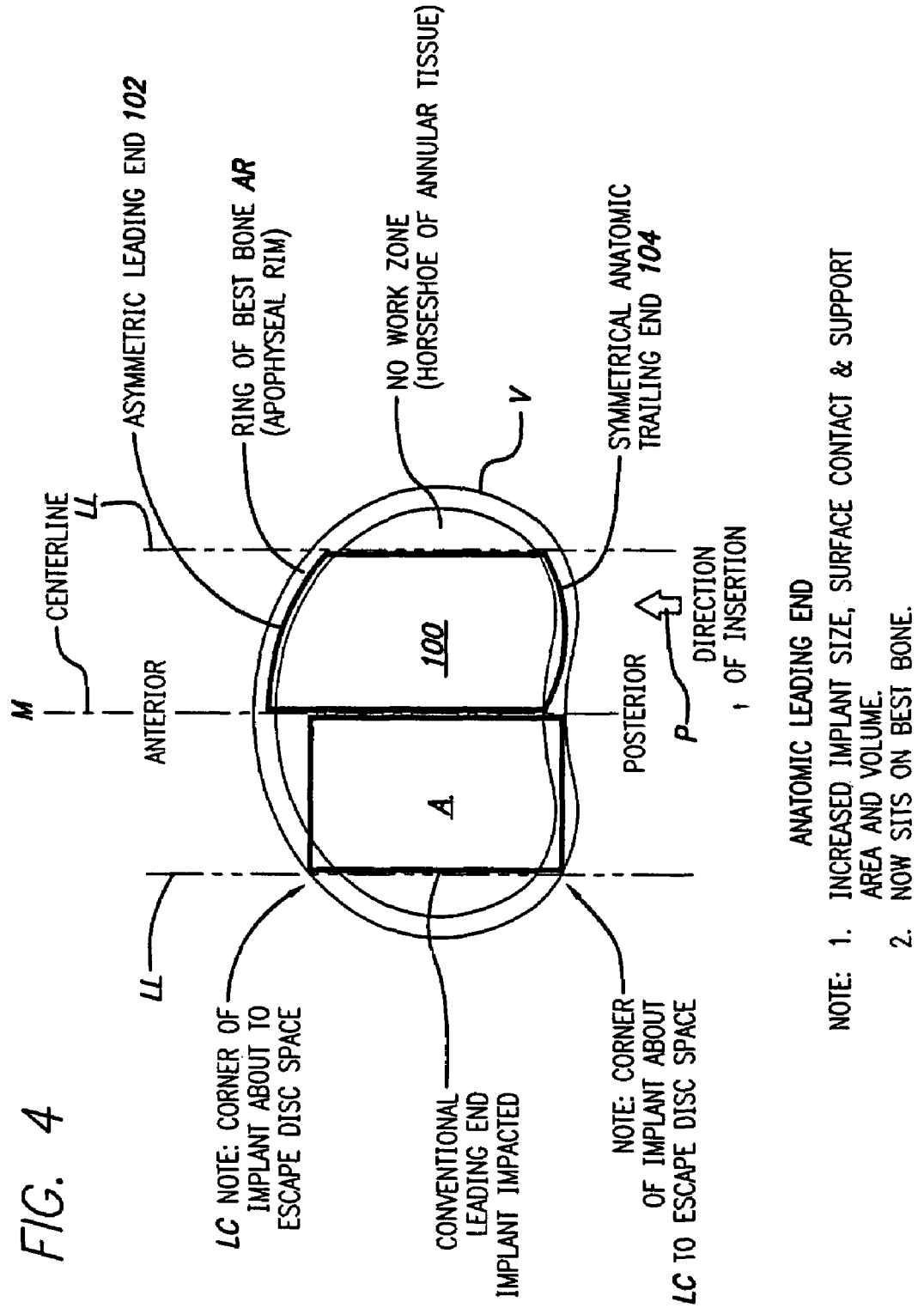
FIG. 4 is a top plan view of an endplate region of a vertebral body with a prior art implant on the left side of the center line and an implant in accordance with one embodiment of the present invention on the right side of the centerline inserted from the posterior aspect of the spine.

FIG. 4 shows an embodiment of the present invention comprising an interbody spinal implant generally referred by the numeral 100, inserted in the direction of arrow P from the posterior aspect of a vertebral body V on one side of the centerline M in the lumbar spine. Implant 100 has a leading end 102 for insertion into the disc space and an opposite trailing end 104. In a preferred embodiment, leading end 102 is configured to not extend beyond the outer dimensions of the two vertebral bodies adjacent the disc space proximate leading end 102 after implant 100 is installed, to maximize the area of contact of the implant with the vertebral bone. Leading end 102 could be described as being generally configured to generally conform to at least a portion of the natural anatomical curvature of the aspect of the vertebral bodies adjacent the disc space proximate leading end 102 after implant 100 is installed. The general configuration of leading end 102 is further described in connection with FIGS. 9A and 9B below.

Figure 7:
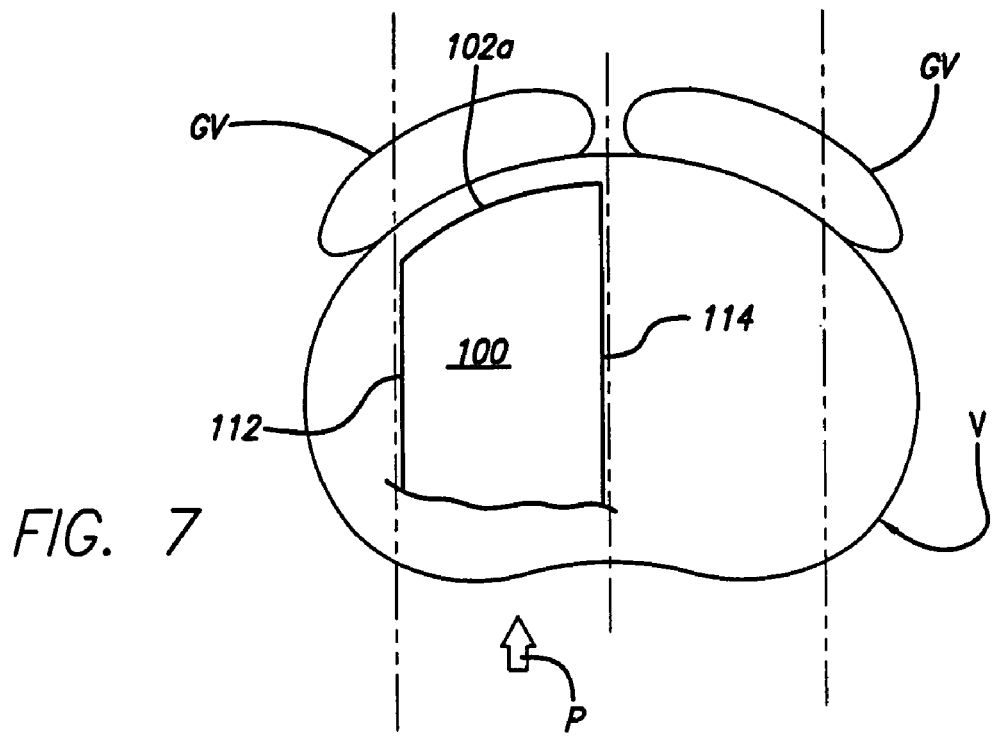
FIG. 7 is a top plan view of a lumbar vertebral body in relationship to the blood vessels located proximate thereto and an implant in accordance with one embodiment of the present invention inserted from the posterior aspect of the vertebral body.
Figure 8:
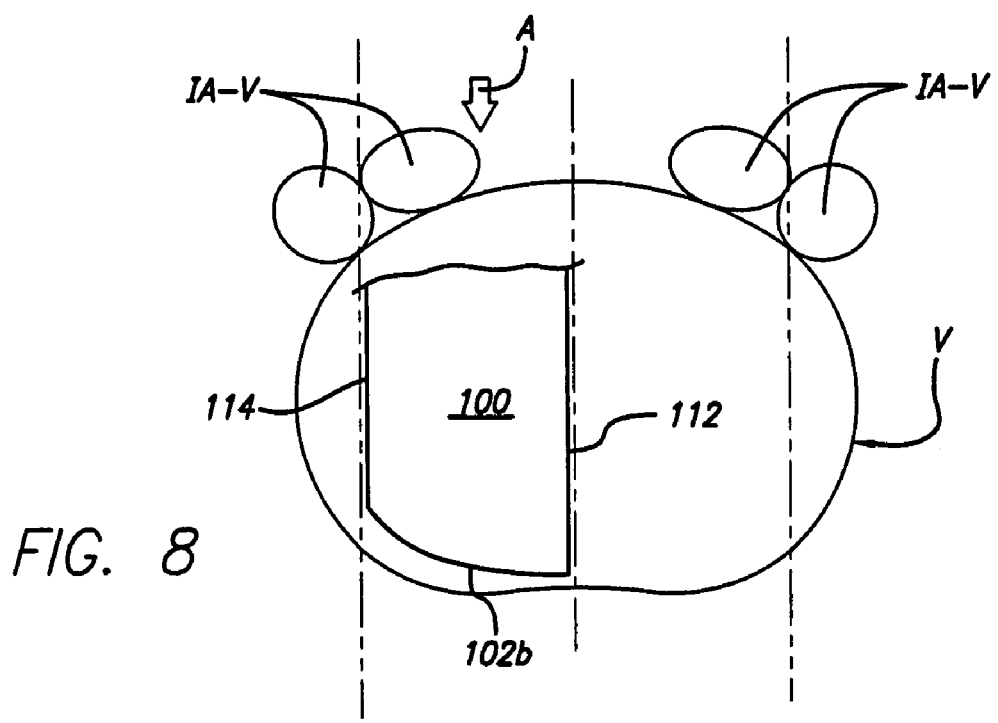
FIG. 8 is a top plan view of a lumbar vertebral body in relationship to the blood vessels located proximate thereto and an implant in accordance with one embodiment of the present invention inserted from the anterior aspect of the vertebral body.

As shown in FIGS. 7 and 8, depending on the direction of insertion, for example, when implant 100 is installed in the direction of arrow P from the posterior aspect of the vertebral body V, leading end 102a is adapted to conform to at least a portion of the anterior aspect of the vertebral body V. When implant 100 is installed in the direction of arrow A from the anterior aspect of vertebral body V, leading end 102b is adapted to conform to at least a portion of the posterior aspect of vertebral body V. Trailing end 104 may be symmetrical or asymmetrical from side-to-side along the transverse axis of the implant and can conform to at least a portion of the natural curvature of the aspect of vertebral body V opposite to leading end 102. Trailing end 104 may or may not be configured to conform to the aspect of vertebral body V proximate trailing end 104 after implant 100 is installed. Trailing end 104 need only have a configuration suitable for its intended use in the spine.

As shown in FIGS. 5, 6A, and 6B, implant 100 has opposed portions 106 and 108 that are adapted to contact and support adjacent vertebral bodies when inserted across the intervertebral space. In this embodiment, opposed portions 106, 108 have a non-arcuate configuration transverse to the longitudinal axis of implant 100 along at least a portion of the length of implant 100. Opposed portions 106, 108 are spaced apart and connected by an interior side wall 112 and an exterior side wall 114 opposite interior side wall 112. Interior side wall 112 is the portion of implant 100 adapted to be placed toward another implant when implant 100 is inserted in pairs into the disc space between the adjacent vertebral bodies to be fused. Interior side wall 112 is not the internal surface of a hollow interior of implant 100. Exterior side wall 114 is adapted to be placed into the disc space nearer to the perimeter of the vertebral bodies than interior side wall 112. Side walls 112, 114 may also include at least one opening for permitting for the growth of bone therethrough.

Preferably, each of the opposed portions 106,108 have at least one opening 110 in communication with one another to permit for the growth of bone in continuity from adjacent vertebral body to adjacent vertebral body and through implant 100. Implant 100 may further be hollow or at least in part hollow. Implant 100 may also include surface roughenings on for example, at least a portion of opposed portions 106,108 for engaging the bone of the adjacent vertebral bodies.

Figure 9A:
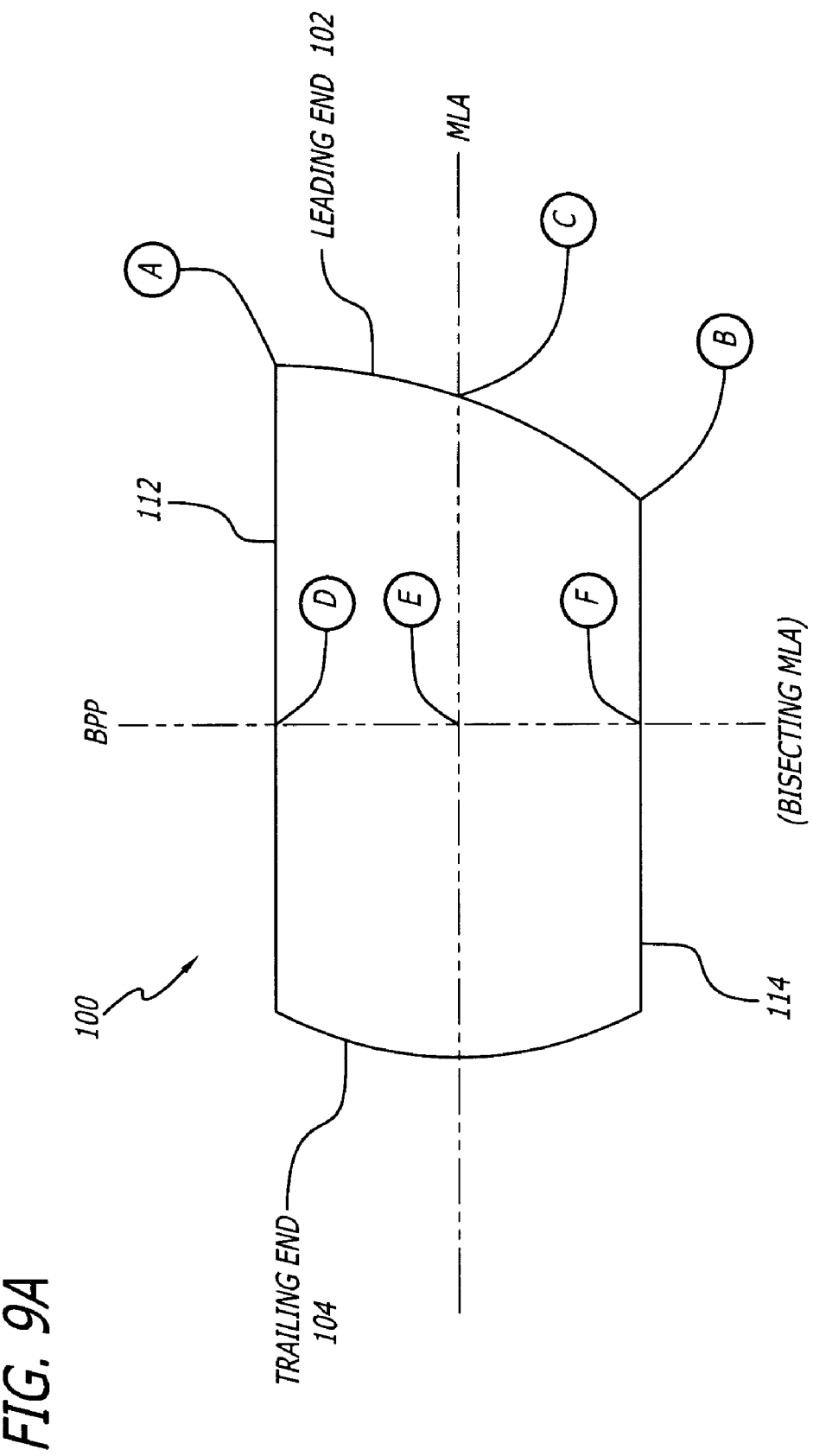
FIG. 9A is a top plan view of an implant in accordance with one embodiment of the present invention illustrating the mid-longitudinal axis and a plane bisecting the mid-longitudinal axis along the length of the implant.
Figure 9B:
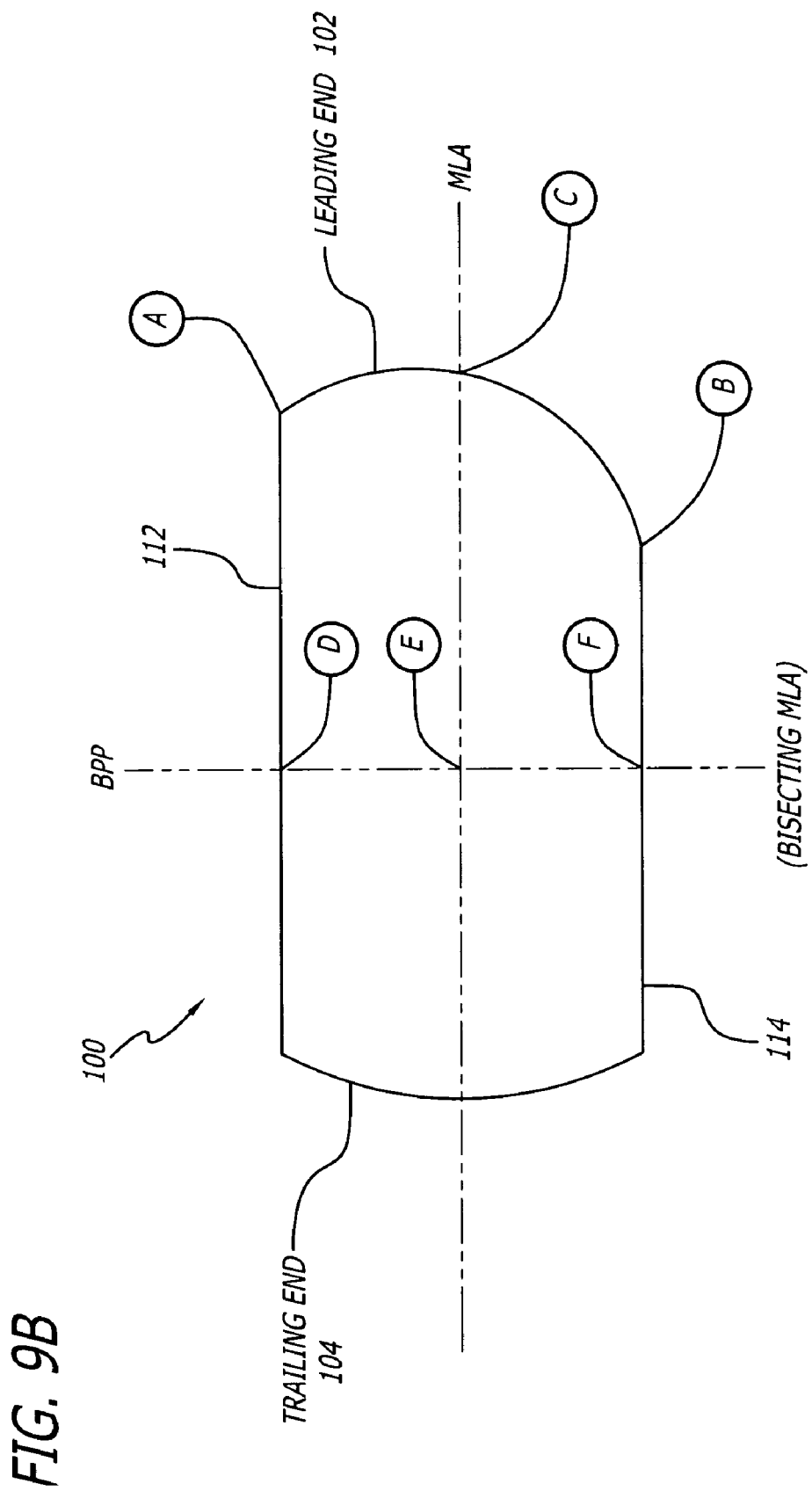
FIG. 9B is a top plan view of an implant in accordance with another embodiment of the present invention illustrating the mid-longitudinal axis and a plane bisecting the mid-longitudinal axis along the length of the implant.

As illustrated in FIG. 9A, implant 100 has a mid-longitudinal axis MLA along its length. Mid-longitudinal axis MLA is bisected by a plane BPP perpendicular to and bisecting the length of implant 100 along the mid-longitudinal axis MLA. Implant 100 has a first distance as measured from point C at leading end 102 to bisecting perpendicular plane BPP at point E that is greater than a second distance as measured from bisecting perpendicular plane BPP at point F to the junction of leading end 102 and exterior side wall 114 at point B. Implant 100 has a third distance as measured from point A at the junction of leading end 102 and interior side wall 112 to bisecting perpendicular plane BPP at point D that is greater than the second distance as measured from point F to point B. While in the preferred embodiment as shown in FIG. 9A, the third distance from points A to D is illustrated as being longer than the first distance from points C to E, the third distance can be equal to or less than the first distance, such as shown in FIG. 9B. In a preferred embodiment, the first distance measured from points C to E is greater than the second distance measured from points B to F; the third distance measured from points A to D can be less than the first distance measured from points C to E; and the third distance measured from points A to D does not equal the second distance measured from points B to F.

In a preferred embodiment of the present invention, when implant 100 is inserted between two adjacent vertebral bodies, implant 100 is contained completely within the vertebral bodies so as not to protrude from the spine. Specifically, the most lateral aspect of the implanted implant at the leading end has been relieved, foreshortened, or contoured so as to allow the remainder of the implant to be safely enlarged so as to be larger overall than the prior implants without the leading end lateral wall protruding from the disc space. Although overall enlargement of the implant is a preferred feature of one embodiment of the present invention, it is not a requisite element of the invention.

Figure 10:
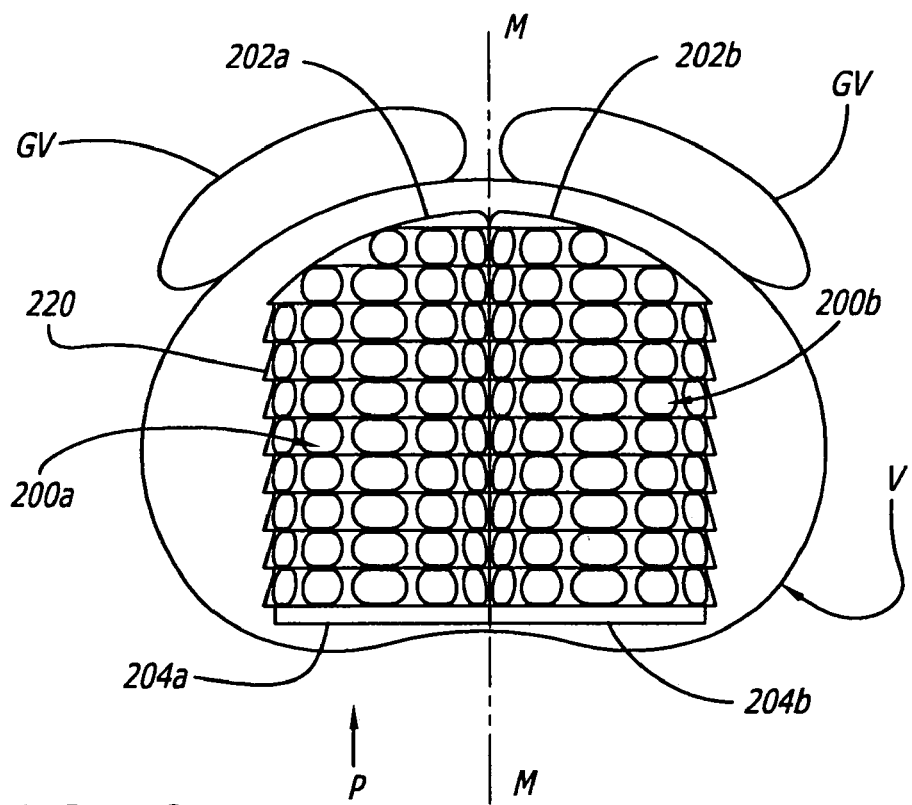
FIG. 10 is a top plan view of a lumbar vertebral body in relationship to the blood vessels located proximate thereto and an implant having arcuate upper and lower opposed portions in accordance with an embodiment of the present invention inserted from the posterior aspect of the vertebral body.

While a preferred embodiment of the present invention has been illustrated and described herein in the form of an implant having non-arcuate upper and lower portions along a portion of the length of the implant, another preferred embodiment of the present invention as best shown in FIG. 10 includes an implant having arcuate upper and lower portions along at least a portion of the length of the implant. All of the features described in association with the non-arcuate embodiments are equally applicable to the arcuate embodiments of the present invention.

Figure 11:
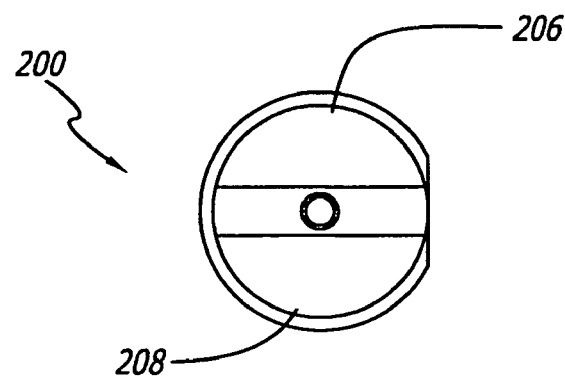
FIG. 11 is a trailing end view of a spinal implant shown in FIG. 10.

FIGS. 10-11 show two interbody spinal implants generally referred to by the numeral 200, inserted in the direction of arrow P from the posterior aspect of a vertebral body V, one on either side of the centerline M in the lumbar spine. Implant 200 is non-threaded and is configured for linear insertion into the disc space in a direction along the mid-longitudinal axis of implant 200. Implant 200 has a leading end 202 for insertion into the disc space and an opposite trailing end 204. In a preferred embodiment, leading end 202 is configured to not extend beyond the outer dimensions of the two vertebral bodies adjacent the disc space proximate leading end 202 after implant 200 is installed, to maximize the area of contact of the implant with the vertebral bone. Leading end 202 could be described as being generally configured to generally conform to at least a portion of the natural anatomical curvature of the aspect of the vertebral bodies adjacent the disc space proximate leading end 202 after implant 200 is installed. In a preferred embodiment, less than half of asymmetric leading end 202 is along a line perpendicular to the mid-longitudinal axis of the implant in a plane dividing the implant into an upper half and a lower half.

In a further preferred embodiment of either arcuate or non-arcuate implants, more than half of the leading end can be a contour that goes from the exterior side wall toward the mid-longitudinal axis of the implant in the plane dividing the implant into an upper half and a lower half. In another preferred embodiment of either arcuate or non-arcuate implants, the leading end includes a curve that extends from the exterior side wall beyond the mid-longitudinal axis of the implant. The more pronounced curve of the leading end of the implant of the present invention as compared to the chamfer of related art implants advantageously provides for closer placement of the implant's leading end to the perimeter of the vertebral body, without the limiting corner protruding therefrom, to more fully utilize the dense cortical bone in the perimeter of the vertebral bodies. The configuration of the implant of the present invention provides the use of an implant having a longer overall length as measured from leading end to trailing end for a better fill of the disc space. Implant 200 has opposed portions 206 and 208 that are arcuate transverse to the longitudinal axis of implant 200 along at least a portion of the length of implant 200 and are adapted to contact and support adjacent vertebral bodies when inserted across the intervertebral space and into the vertebral bodies. Implant 200 can further include protrusions or surface roughenings such as ratchetings 220 for enhancing stability. Surface roughenings may also include ridges, knurling and the like.

The present invention is not limited to use in the lumbar spine and is useful throughout the spine. In regard to use in the cervical spine, by way of example, in addition to various blood vessels the esophagus and trachea also should be avoided.

Further, the implant of the present invention preferably includes non-arcuate opposed surface portions that are either generally parallel to one another along the length of the implant or in angular relationship to each other such that the opposed surfaces are closer to each other proximate one end of the implant than at the longitudinally opposite other. For example, at least a portion of the opposed surfaces may be in a diverging relationship to each other from the trailing end to the leading end for allowing angulation of the adjacent vertebral bodies relative to each other. Alternatively, at least a portion of the opposed surfaces may be generally in a converging relationship to each other from the trailing end to the leading end for allowing angulation of the adjacent vertebral bodies relative to each other. The spinal implant of the present invention allows for a variable surface, or any other configuration and relationship of the opposed surfaces.

While the exact contour and/or curvature of a particular vertebral body may not be known, the teaching of having the implant leading end be arcuate or truncated along one side (the lateral leading end) or from side to side so as to eliminate the length limiting lateral leading corner LC or the side wall or lateral aspect junction to the implant leading end is of such benefit that minor differences do not detract from its utility. Further, the range of describable curvatures may be varied proportionately with the size of the implants as well as their intended location within the spine and direction of insertion to be most appropriate and is easily determinable by those of ordinary skill in the art.

Generally for use in the lumbar spine, when the leading end of the implant is a portion of a circle then the arc of radius of the curvature of the leading end of the implant should be from 10-30 mm to be of greatest benefit, though it could be greater or less, and still be beneficial. The same is true for the cervical spine where the arc of radius is preferably 8-20 mm. While particular preferred embodiments of the present invention have been shown and described, it will be obvious to those skilled in the art that changes and modifications may be made without departing from this invention in its broader aspects.

While specific innovative features were presented in reference to specific examples, they are just examples, and it should be understood that various combinations of these innovative features beyond those specifically shown are taught such that they may now be easily alternatively combined and are hereby anticipated and claimed.

What is claimed is:

1. An artificial interbody spinal implant for insertion at least in part across the surgically corrected height of a disc space between adjacent vertebral bodies of a human spine, the vertebral bodies having an anterior aspect and a posterior aspect, said implant comprising:

a leading end for insertion first into the disc space, a trailing end opposite said leading end, and therebetween a length along a mid-longitudinal axis of said implant, said leading end being asymmetrical;

opposed portions between said leading and trailing ends adapted to be placed within the disc space to contact and support the adjacent vertebral bodies, said opposed portions being non-arcuate along at least a portion of the length of said implant, each of said opposed portions having at least one opening therein to permit for the growth of bone from adjacent vertebral body to adjacent vertebral body through said implant, said implant being formed at least in part of a material other than bone, said material comprising at least one of surgical quality titanium and its alloys, cobalt chrome alloy, tantalum, any metal or alloy suitable for the intended purpose, any ceramic material suitable for the intended purpose, and any plastic or composite material suitable for the intended purpose;

an interior facing side wall, an exterior facing side wall opposite said interior facing side wall, and a width therebetween, said interior and exterior facing side walls extending between said opposed portions and having an inner surface facing each other, said exterior facing side wall including a straight portion along the length of said implant, said width of said implant being less than approximately one-half of the maximum width of the adjacent vertebral bodies into which said implant is adapted to be inserted, said interior and exterior facing side walls being between said opposed portions and said leading and trailing ends, said interior facing side wall adapted to be oriented toward another implant when inserted within the disc space, each of said opposed portions having a vertebral body contacting surface between said at least one opening and at least one of said interior side wall and said exterior side wall, each of said vertebral body contacting surfaces being adapted to be placed toward one of the adjacent vertebral bodies, said opposed portions being spaced apart and said inner surfaces of said interior and exterior facing side walls being spaced apart to define a hollow interior in communication with said openings, each of said at least one openings of said opposed portions having a mid-longitudinal axis and a maximum dimension in a plane perpendicular to the mid-longitudinal axis of each of said openings, said hollow interior having a maximum dimension between said inner surfaces of said interior and exterior facing side walls and in a plane perpendicular to the mid-longitudinal axis of said openings greater than said maximum dimension of said opening;

a first distance as measured along the mid-longitudinal axis of said implant from an intersection of said leading end and the mid-longitudinal axis of said implant to an intersection of the mid-longitudinal axis of said implant and a plane perpendicular to and bisecting the length along the mid-longitudinal axis of said implant, said first distance being greater than a second distance as measured along the mid-longitudinal axis of said implant from an intersection of said perpendicular plane and said exterior side wall to a junction of said leading end and said exterior side wall; and a third distance as measured along the mid-longitudinal axis of said implant from a junction of said leading end and said interior side wall to an intersection of said interior side wall and said perpendicular plane, said third distance being greater than said second distance, said first distance being greater than said third distance, said leading end including a curved portion extending from the junction of said leading end and said exterior side wall to at least the intersection of said leading end and the mid-longitudinal axis of said implant.

2. The implant of claim 1, wherein said first distance and said third distance are approximately equal.

3. The implant of claim 1, wherein said leading end is at least in part non-linear.

4. The implant of claim 1, wherein at least a portion of said leading end is tapered from opposed portion to opposed portion for facilitating insertion of said implant between the two adjacent vertebral bodies.

5. The implant of claim 1, wherein less than half of said leading end is along a line perpendicular to the mid-longitudinal axis of said implant in a plane dividing said implant into an upper half and a lower half.

6. The implant of claim 1, further comprising at least one protrusion extending from at least one of said opposed portions for engaging at least one of the adjacent vertebral bodies to maintain said implant within the disc space.

7. The implant of claim 6, wherein said protrusion comprises a ridge.

8. The implant of claim 1, further comprising a plurality of surface roughenings for engaging the adjacent vertebral bodies and for maintaining said implant in place, said surface roughenings being present on at least a part of said opposed portions.

9. The implant of claim 1, wherein said opposed portions have a porous surface.

10. The implant of claim 1, wherein said opposed portions have a bone ingrowth surface.

11. The implant of claim 1, wherein said implant has surface protrusions configured to protrude into bone.

12. The implant of claim 1, wherein said implant material is porous.

13. The implant of claim 1, in combination with a fusion promoting material other than bone.

14. The implant of claim 1, wherein said implant comprises a bone ingrowth material other than bone.

15. The implant of claim 1, further comprising a material that intrinsically participates in the growth of bone from one of the adjacent vertebral bodies to the other of the adjacent vertebral bodies.

16. The implant of claim 1, wherein said implant is treated with a fusion promoting substance.

17. The implant of claim 16, wherein said fusion promoting substance is bone morphogenetic protein.

18. The implant of claim 1, wherein said implant material is stronger than cancellous bone.

19. The implant of claim 1, wherein said implant material is stronger than cortical bone.

20. The implant of claim 1, wherein at least a portion of said implant is bioresorbable.

21. The implant of claim 1, further in combination with bone morphogenetic protein.

22. The implant of claim 1, further in combination with an osteogenic material.

23. The implant of claim 22, wherein said osteogenic material is a material other than bone.

24. The implant of claim 22, wherein said material is genetic material coding for the production of bone.

25. The implant of claim 22, wherein said material is bone morphogenetic protein.

26. The implant of claim 1, further in combination with genetic material coding for production of bone.

27. The implant of claim 1, wherein said implant has a maximum length less than and approximating the posterior to anterior depth of the vertebral body.

28. The implant of claim 1, wherein said trailing end is adapted to conform from side to side to at least a portion of the peripheral contour of at least one of the anterior and posterior aspects of the vertebral bodies adjacent a disc space into which said implant is inserted.

29. The implant of claim 1, wherein said opposed portions have at least two openings therein.

30. The implant of claim 1, wherein at least a portion of said opposed portions are in a diverging relationship to each other from trailing end to leading end for allowing angulation of the adjacent vertebral bodies relative to each other.

31. The implant of claim 1, wherein at least a portion of said opposed portions are generally in a converging relationship to each other from trailing end to leading end for allowing angulation of the adjacent vertebral bodies relative to each other.

32. The implant of claim 1, further comprising a plurality of openings and passages for retaining fusion promoting substance.

33. The implant of claim 1, wherein said implant is adapted for insertion from the posterior aspect of the vertebral bodies and said leading end is configured to conform to the anatomic contour of at least a portion of the anterior aspect of the vertebral bodies.

34. The implant of claim 1, wherein said implant is adapted for insertion from the anterior aspect of the vertebral bodies and said leading end is configured to conform to the anatomic contour of at least a portion of the posterior aspect of the vertebral bodies.

35. The implant of claim 1, wherein said implant is adapted for insertion from a first lateral aspect of the vertebral bodies and said leading end is configured to conform to the anatomic contour of at least a portion of a second lateral aspect of the vertebral bodies opposite the first lateral aspect.

36. The implant of claim 1, further in combination with hydroxyapatite.

37. The implant of claim 1, wherein said interior and exterior facing side walls are substantially parallel to one another along a majority of the length of said implant.

38. The implant of claim 1, wherein said interior and exterior facing side walls are generally positioned the same distance from the mid-longitudinal axis of the implant along a substantial portion of the length of said implant.

39. The implant of claim 1, wherein said vertebral body contacting surfaces each have a maximum width transverse to the mid-longitudinal axis of said implant, each of said interior and exterior facing side walls having a maximum thickness transverse to the mid-longitudinal axis of said implant, the maximum thickness of at least one of said side walls being less than the maximum width of at least one of said vertebral body contacting surfaces.

40. The implant of claim 1, wherein said trailing end is generally symmetrical relative to the mid-longitudinal axis.

41. The implant of claim 1, wherein said leading and trailing ends each have a radius of curvature, the radius of curvature of said leading end being different from the radius of curvature of said trailing end.

42. The implant of claim 41, wherein the radius of curvature of said leading end is greater than the radius of curvature of said trailing end.

* * * * *

UNITED STATES PATENT AND TRADEMARK OFFICE
CERTIFICATE OF CORRECTION

PATENT NO.       : 7,462,195 B1
APPLICATION NO.  : 09/553573
DATED            : December 9, 2008
INVENTOR(S)      : Gary K. Michelson It is certified that error appears in the above-identified patent and that said Letters Patent is hereby corrected as shown below:

On the Title Page:
Item (54) Title, line 1: after "LUMBAR" insert -- NON-ARCUATE --; and
Item (74) Attorney, Agent or Firm: change "Ferrano" to -- Ferraro --.

On the Title Page, Page 2, Other Publications:
Item 56 line 41: change "171-172" to -- 171-182 --.

Signed and Sealed this

Tenth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO.        : 7,462,195 B1
APPLICATION NO. : 09/553573
DATED             : December 9, 2008
INVENTOR(S)       : Gary K. Michelson It is certified that error appears in the above-identified patent and that said Letters Patent is hereby corrected as shown below:

On the Title Page:
Item (54) Title, line 1: after "LUMBAR" insert -- NON-ARCUATE --; and
Item (74) Attorney, Agent or Firm: change "Ferrano" to -- Ferraro --.

On the Title Page, Page 2, Other Publications:
Item 56 line 41: change "171-172" to -- 171-182 --.

Column 1, line 1, after "LUMBAR" insert -- NON-ARCUATE --.

This certificate supersedes the Certificate of Correction issued February 10, 2009.

Signed and Sealed this

Tenth Day of March, 2009

JOHN DOLL
*Acting Director of the United States Patent and Trademark Office*